(12) United States Patent
Campbell

(10) Patent No.: US 8,092,993 B2
(45) Date of Patent: Jan. 10, 2012

(54) HYDROGEL THIN FILM FOR USE AS A BIOSENSOR

(75) Inventor: Shannon E. Campbell, Boulder, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 68 days.

(21) Appl. No.: 12/338,806

(22) Filed: Dec. 18, 2008

(65) Prior Publication Data

US 2009/0170124 A1    Jul. 2, 2009

Related U.S. Application Data

(60) Provisional application No. 61/009,721, filed on Dec. 31, 2007.

(51) Int. Cl.
*C12Q 1/68* (2006.01)
*G01N 33/53* (2006.01)

(52) U.S. Cl. .................. 435/6; 435/7.1; 435/7.2

(58) Field of Classification Search .......... None
See application file for complete search history.

(56) References Cited

U.S. PATENT DOCUMENTS

| | | | |
|---|---|---|---|
| 3,638,640 A | 2/1972 | Shaw | |
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,936,679 A | 6/1990 | Mersch | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,972,331 A | 11/1990 | Chance | |

(Continued)

FOREIGN PATENT DOCUMENTS

EP       0615723       9/1994

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997). Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

East, Christine E., et al.; "Fetal Oxygen Saturation and Uterine Contractions During Labor," *American Journal of Perinatology*, vol. 15, No. 6, pp. 345-349 (Jun. 1998).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

(Continued)

*Primary Examiner* — Mark Navarro
(74) *Attorney, Agent, or Firm* — Fletcher Yoder

(57) ABSTRACT

The present disclosure provides a biosensor capable of producing an indicator response upon detection of the presence of certain metabolites in a biological sample. The biosensor includes a hydrogel that is functionalized with affinity molecules specific to markers for one or more pathogens. The biosensor also includes a detection system adapted to detect the binding the pathogen-specific markers with their corresponding affinity molecules.

15 Claims, 2 Drawing Sheets

U.S. PATENT DOCUMENTS

| | | | |
|---|---|---|---|
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |

| | | | | | |
|---|---|---|---|---|---|
| 5,564,417 A | 10/1996 | Chance | 5,807,248 A | 9/1998 | Mills |
| 5,575,284 A | 11/1996 | Athan et al. | 5,810,723 A | 9/1998 | Aldrich |
| 5,575,285 A | 11/1996 | Takanashi et al. | 5,810,724 A | 9/1998 | Gronvall |
| 5,577,500 A | 11/1996 | Potratz | 5,813,980 A | 9/1998 | Levinson et al. |
| 5,582,169 A | 12/1996 | Oda et al. | 5,817,008 A | 10/1998 | Rafert et al. |
| 5,584,296 A | 12/1996 | Cui et al. | 5,817,009 A | 10/1998 | Rosenheimer et al. |
| 5,588,425 A | 12/1996 | Sackner et al. | 5,817,010 A | 10/1998 | Hibl |
| 5,588,427 A | 12/1996 | Tien | 5,818,985 A | 10/1998 | Merchant et al. |
| 5,590,652 A | 1/1997 | Inai | 5,820,550 A | 10/1998 | Polson et al. |
| 5,595,176 A | 1/1997 | Yamaura | 5,823,950 A | 10/1998 | Diab et al. |
| 5,596,986 A | 1/1997 | Goldfarb | 5,823,952 A | 10/1998 | Levinson et al. |
| 5,611,337 A | 3/1997 | Bukta | 5,827,182 A | 10/1998 | Raley et al. |
| 5,617,852 A | 4/1997 | MacGregor | 5,830,135 A | 11/1998 | Bosque et al. |
| 5,619,992 A | 4/1997 | Guthrie et al. | 5,830,136 A | 11/1998 | Delonzor et al. |
| 5,626,140 A | 5/1997 | Feldman et al. | 5,830,137 A | 11/1998 | Scharf |
| 5,630,413 A | 5/1997 | Thomas et al. | 5,830,139 A | 11/1998 | Abreu |
| 5,632,272 A | 5/1997 | Diab et al. | 5,831,598 A | 11/1998 | Kauffert et al. |
| 5,632,273 A | 5/1997 | Suzuki | 5,839,439 A | 11/1998 | Nierlich et al. |
| 5,634,459 A | 6/1997 | Gardosi | RE36,000 E | 12/1998 | Swedlow et al. |
| 5,638,593 A | 6/1997 | Gerhardt et al. | 5,842,979 A | 12/1998 | Jarman et al. |
| 5,638,818 A | 6/1997 | Diab et al. | 5,842,981 A | 12/1998 | Larsen et al. |
| 5,645,059 A | 7/1997 | Fein et al. | 5,842,982 A | 12/1998 | Mannheimer |
| 5,645,060 A | 7/1997 | Yorkey et al. | 5,846,190 A | 12/1998 | Woehrle |
| 5,645,440 A | 7/1997 | Tobler et al. | 5,851,178 A | 12/1998 | Aronow |
| 5,660,567 A | 8/1997 | Nierlich et al. | 5,851,179 A | 12/1998 | Ritson et al. |
| 5,662,105 A | 9/1997 | Tien | 5,853,364 A | 12/1998 | Baker, Jr. et al. |
| 5,662,106 A | 9/1997 | Swedlow et al. | 5,860,919 A | 1/1999 | Kiani-Azarbayjany et al. |
| 5,666,952 A | 9/1997 | Fuse et al. | 5,865,736 A | 2/1999 | Baker, Jr. et al. |
| 5,671,529 A | 9/1997 | Nelson | 5,871,442 A | 2/1999 | Madarasz et al. |
| 5,673,692 A | 10/1997 | Schulze et al. | 5,873,821 A | 2/1999 | Chance et al. |
| 5,673,693 A | 10/1997 | Solenberger | 5,879,294 A | 3/1999 | Anderson et al. |
| 5,676,139 A | 10/1997 | Goldberger et al. | 5,885,213 A | 3/1999 | Richardson et al. |
| 5,676,141 A | 10/1997 | Hollub | 5,890,929 A | 4/1999 | Mills et al. |
| 5,678,544 A | 10/1997 | DeLonzor et al. | 5,891,021 A | 4/1999 | Dillon et al. |
| 5,680,857 A | 10/1997 | Pelikan et al. | 5,891,022 A | 4/1999 | Pologe |
| 5,685,299 A | 11/1997 | Diab et al. | 5,891,024 A | 4/1999 | Jarman et al. |
| 5,685,301 A | 11/1997 | Klomhaus | 5,891,025 A | 4/1999 | Buschmann et al. |
| 5,687,719 A | 11/1997 | Sato et al. | 5,891,026 A | 4/1999 | Wang et al. |
| 5,687,722 A | 11/1997 | Tien et al. | 5,902,235 A | 5/1999 | Lewis et al. |
| 5,692,503 A | 12/1997 | Kuenstner | 5,910,108 A | 6/1999 | Solenberger |
| 5,692,505 A | 12/1997 | Fouts | 5,911,690 A | 6/1999 | Rall |
| 5,709,205 A | 1/1998 | Bukta | 5,912,656 A | 6/1999 | Tham et al. |
| 5,713,355 A | 2/1998 | Richardson et al. | 5,913,819 A | 6/1999 | Taylor et al. |
| 5,724,967 A | 3/1998 | Venkatachalam | 5,916,154 A | 6/1999 | Hobbs et al. |
| 5,727,547 A | 3/1998 | Levinson et al. | 5,916,155 A | 6/1999 | Levinson et al. |
| 5,730,124 A | 3/1998 | Yamauchi | 5,919,133 A | 7/1999 | Taylor et al. |
| 5,731,582 A | 3/1998 | West | 5,919,134 A | 7/1999 | Diab |
| D393,830 S | 4/1998 | Tobler et al. | 5,920,263 A | 7/1999 | Huttenhoff et al. |
| 5,743,260 A | 4/1998 | Chung et al. | 5,921,921 A | 7/1999 | Potratz et al. |
| 5,743,263 A | 4/1998 | Baker, Jr. | 5,922,607 A | 7/1999 | Bernreuter |
| 5,746,206 A | 5/1998 | Mannheimer | 5,924,979 A | 7/1999 | Swedlow et al. |
| 5,746,697 A | 5/1998 | Swedlow et al. | 5,924,980 A | 7/1999 | Coetzee |
| 5,752,914 A | 5/1998 | Delonzor et al. | 5,924,982 A | 7/1999 | Chin |
| 5,755,226 A | 5/1998 | Carim et al. | 5,924,985 A | 7/1999 | Jones |
| 5,758,644 A | 6/1998 | Diab et al. | 5,934,277 A | 8/1999 | Mortz |
| 5,760,910 A | 6/1998 | Lepper, Jr. et al. | 5,934,925 A | 8/1999 | Tobler et al. |
| 5,766,125 A | 6/1998 | Aoyagi et al. | 5,940,182 A | 8/1999 | Lepper, Jr. et al. |
| 5,766,127 A | 6/1998 | Pologe et al. | 5,954,644 A | 9/1999 | Dettling et al. |
| 5,769,785 A | 6/1998 | Diab et al. | 5,960,610 A | 10/1999 | Levinson et al. |
| 5,772,587 A | 6/1998 | Gratton et al. | 5,961,450 A | 10/1999 | Merchant et al. |
| 5,774,213 A | 6/1998 | Trebino et al. | 5,961,452 A | 10/1999 | Chung et al. |
| 5,776,058 A | 7/1998 | Levinson et al. | 5,964,701 A | 10/1999 | Asada et al. |
| 5,776,059 A | 7/1998 | Kaestle | 5,971,930 A | 10/1999 | Elghazzawi |
| 5,779,630 A | 7/1998 | Fein et al. | 5,978,691 A | 11/1999 | Mills |
| 5,779,631 A | 7/1998 | Chance | 5,978,693 A | 11/1999 | Hamilton et al. |
| 5,782,237 A | 7/1998 | Casciani et al. | 5,983,122 A | 11/1999 | Jarman et al. |
| 5,782,756 A | 7/1998 | Mannheimer | 5,987,343 A | 11/1999 | Kinast |
| 5,782,757 A | 7/1998 | Diab et al. | 5,991,648 A | 11/1999 | Levin |
| 5,782,758 A | 7/1998 | Ausec et al. | 5,995,855 A | 11/1999 | Kiani et al. |
| 5,786,592 A | 7/1998 | Hök | 5,995,856 A | 11/1999 | Mannheimer et al. |
| 5,790,729 A | 8/1998 | Pologe et al. | 5,995,858 A | 11/1999 | Kinast |
| 5,792,052 A | 8/1998 | Isaacson et al. | 5,995,859 A | 11/1999 | Takahashi |
| 5,795,292 A | 8/1998 | Lewis et al. | 5,997,343 A | 12/1999 | Mills et al. |
| 5,797,841 A | 8/1998 | Delonzor et al. | 5,999,834 A | 12/1999 | Wang et al. |
| 5,800,348 A | 9/1998 | Kaestle | 6,002,952 A | 12/1999 | Diab et al. |
| 5,800,349 A | 9/1998 | Isaacson et al. | 6,005,658 A | 12/1999 | Kaluza et al. |
| 5,803,910 A | 9/1998 | Potratz | 6,006,120 A | 12/1999 | Levin |
| 5,807,246 A | 9/1998 | Sakaguchi et al. | 6,011,985 A | 1/2000 | Athan et al. |
| 5,807,247 A | 9/1998 | Merchant et al. | 6,011,986 A | 1/2000 | Diab et al. |

| | | |
|---|---|---|
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,120,460 A | 9/2000 | Abreu |
| 6,122,535 A | 9/2000 | Kaestle et al. |
| 6,133,994 A | 10/2000 | Mathews et al. |
| 6,134,460 A | 10/2000 | Chance |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,312,393 B1 | 11/2001 | Abreu |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,487,439 B1 | 11/2002 | Skladnev et al. |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |

| | | |
|---|---|---|
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,042 B1 | 9/2003 | Powell |
| 6,618,602 B2 | 9/2003 | Levin et al. |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,690,958 B1 | 2/2004 | Walker et al. |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,048 B1 | 3/2004 | Chance |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,245 B1 | 3/2004 | Ono |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,274 B2 | 5/2004 | Powell |
| 6,731,963 B2 | 5/2004 | Finarov et al. |
| 6,731,967 B1 | 5/2004 | Turcott |
| 6,735,459 B2 | 5/2004 | Parker |
| 6,738,141 B1 * | 5/2004 | Thirstrup ...................... 356/445 |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,785,568 B2 | 8/2004 | Chance |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,053 B2 | 2/2005 | Daalmans et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |

| Patent | Type | Date | Inventor |
|---|---|---|---|
| 6,898,451 | B2 | 5/2005 | Wuori |
| 6,898,452 | B2 | 5/2005 | Al-Ali et al. |
| 6,909,912 | B2 | 6/2005 | Melker et al. |
| 6,912,413 | B2 | 6/2005 | Rantala et al. |
| 6,916,289 | B2 | 7/2005 | Schnall |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,939,307 | B1 | 9/2005 | Dunlop |
| 6,941,162 | B2 | 9/2005 | Fudge et al. |
| 6,947,780 | B2 | 9/2005 | Scharf |
| 6,947,781 | B2 | 9/2005 | Asada et al. |
| 6,949,081 | B1 | 9/2005 | Chance |
| 6,950,687 | B2 | 9/2005 | Al-Ali |
| 6,961,598 | B2 | 11/2005 | Diab |
| 6,963,767 | B2 | 11/2005 | Rantala et al. |
| 6,971,580 | B2 | 12/2005 | DeLonzor et al. |
| 6,983,178 | B2 | 1/2006 | Fine et al. |
| 6,985,763 | B2 | 1/2006 | Boas et al. |
| 6,985,764 | B2 | 1/2006 | Mason et al. |
| 6,990,426 | B2 | 1/2006 | Yoon et al. |
| 6,992,751 | B2 | 1/2006 | Okita et al. |
| 6,992,772 | B2 | 1/2006 | Block et al. |
| 6,993,371 | B2 | 1/2006 | Kiani et al. |
| 6,993,372 | B2 | 1/2006 | Fine et al. |
| 6,996,427 | B2 | 2/2006 | Ali et al. |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |
| 7,016,715 | B2 | 3/2006 | Stetson |
| 7,020,507 | B2 | 3/2006 | Scharf et al. |
| 7,024,233 | B2 | 4/2006 | Ali et al. |
| 7,024,235 | B2 | 4/2006 | Melker et al. |
| 7,025,728 | B2 | 4/2006 | Ito et al. |
| 7,027,849 | B2 | 4/2006 | Al-Ali |
| 7,027,850 | B2 | 4/2006 | Wasserman |
| 7,030,749 | B2 | 4/2006 | Al-Ali |
| 7,035,697 | B1 | 4/2006 | Brown |
| 7,039,449 | B2 | 5/2006 | Al-Ali |
| 7,043,289 | B2 | 5/2006 | Fine et al. |
| 7,047,054 | B2 | 5/2006 | Benni |
| 7,047,055 | B2 | 5/2006 | Boaz et al. |
| 7,060,035 | B2 | 6/2006 | Wasserman et al. |
| 7,062,307 | B2 | 6/2006 | Norris et al. |
| 7,067,893 | B2 | 6/2006 | Mills et al. |
| 7,072,701 | B2 | 7/2006 | Chen et al. |
| 7,072,702 | B2 | 7/2006 | Edgar, Jr. et al. |
| 7,079,880 | B2 | 7/2006 | Stetson |
| 7,085,597 | B2 | 8/2006 | Fein et al. |
| 7,096,052 | B2 | 8/2006 | Mason et al. |
| 7,096,054 | B2 | 8/2006 | Abdul-Hafiz et al. |
| 7,107,088 | B2 | 9/2006 | Aceti |
| 7,113,815 | B2 | 9/2006 | O'Neil et al. |
| 7,123,950 | B2 | 10/2006 | Mannheimer |
| 7,127,278 | B2 | 10/2006 | Melker et al. |
| 7,130,671 | B2 | 10/2006 | Baker, Jr. et al. |
| 7,132,641 | B2 | 11/2006 | Schulz et al. |
| 7,133,711 | B2 | 11/2006 | Chernoguz et al. |
| 7,139,599 | B2 | 11/2006 | Terry |
| 7,142,901 | B2 | 11/2006 | Kiani et al. |
| 7,162,288 | B2 | 1/2007 | Nordstrom |
| 7,162,306 | B2 | 1/2007 | Caby et al. |
| 7,190,987 | B2 | 3/2007 | Lindekugel et al. |
| 7,198,778 | B2 | 4/2007 | Achilefu et al. |
| 7,209,775 | B2 | 4/2007 | Bae et al. |
| 7,215,984 | B2 | 5/2007 | Diab et al. |
| 7,225,006 | B2 | 5/2007 | Al-Ali et al. |
| 7,236,811 | B2 | 6/2007 | Schmitt |
| 7,236,881 | B2 | 6/2007 | Liu et al. |
| 7,248,910 | B2 | 7/2007 | Li et al. |
| 7,254,433 | B2 | 8/2007 | Diab et al. |
| 7,254,434 | B2 | 8/2007 | Schulz et al. |
| 7,263,395 | B2 | 8/2007 | Chan et al. |
| 7,272,426 | B2 | 9/2007 | Schmid |
| 7,280,858 | B2 | 10/2007 | Al-Ali et al. |
| 7,295,866 | B2 | 11/2007 | Al-Ali et al. |
| 7,305,262 | B2 | 12/2007 | Brodnick et al. |
| 7,313,427 | B2 | 12/2007 | Benni |
| 7,315,753 | B2 | 1/2008 | Baker, Jr. et al. |
| 7,373,193 | B2 | 5/2008 | Al-Ali et al. |
| 2001/0005773 | A1 | 6/2001 | Larsen et al. |
| 2001/0020122 | A1 | 9/2001 | Steuer et al. |
| 2001/0021803 | A1 | 9/2001 | Blank et al. |
| 2001/0039376 | A1 | 11/2001 | Steuer et al. |
| 2001/0044700 | A1 | 11/2001 | Kobayashi et al. |
| 2001/0051767 | A1 | 12/2001 | Williams et al. |
| 2002/0026106 | A1 | 2/2002 | Khalil et al. |
| 2002/0026109 | A1 | 2/2002 | Diab et al. |
| 2002/0028990 | A1 | 3/2002 | Shepherd et al. |
| 2002/0035318 | A1 | 3/2002 | Mannheimer et al. |
| 2002/0038078 | A1 | 3/2002 | Ito |
| 2002/0038079 | A1 | 3/2002 | Steuer et al. |
| 2002/0042558 | A1 | 4/2002 | Mendelson |
| 2002/0049389 | A1 | 4/2002 | Abreu |
| 2002/0062071 | A1 | 5/2002 | Diab et al. |
| 2002/0068859 | A1 | 6/2002 | Knopp |
| 2002/0111748 | A1 | 8/2002 | Kobayashi et al. |
| 2002/0128544 | A1 | 9/2002 | Diab et al. |
| 2002/0133067 | A1 | 9/2002 | Jackson, III |
| 2002/0133068 | A1 | 9/2002 | Huiku |
| 2002/0156354 | A1 | 10/2002 | Larson |
| 2002/0161287 | A1 | 10/2002 | Schmitt |
| 2002/0161290 | A1 | 10/2002 | Chance |
| 2002/0165439 | A1 | 11/2002 | Schmitt |
| 2002/0173706 | A1 | 11/2002 | Takatani |
| 2002/0173709 | A1 | 11/2002 | Fine et al. |
| 2002/0190863 | A1 | 12/2002 | Lynn |
| 2002/0198442 | A1 | 12/2002 | Rantala et al. |
| 2002/0198443 | A1 | 12/2002 | Ting |
| 2003/0018243 | A1 | 1/2003 | Gerhardt et al. |
| 2003/0023140 | A1 | 1/2003 | Chance |
| 2003/0036690 | A1 | 2/2003 | Geddes et al. |
| 2003/0045785 | A1 | 3/2003 | Diab et al. |
| 2003/0055324 | A1 | 3/2003 | Wasserman |
| 2003/0060693 | A1 | 3/2003 | Monfre et al. |
| 2003/0073889 | A1 | 4/2003 | Keilbach et al. |
| 2003/0073890 | A1 | 4/2003 | Hanna |
| 2003/0100840 | A1 | 5/2003 | Sugiura et al. |
| 2003/0132495 | A1 | 7/2003 | Mills et al. |
| 2003/0135099 | A1 | 7/2003 | Al-Ali |
| 2003/0139687 | A1 | 7/2003 | Abreu |
| 2003/0144584 | A1 | 7/2003 | Mendelson |
| 2003/0162414 | A1 | 8/2003 | Schulz et al. |
| 2003/0171662 | A1 | 9/2003 | O'Connor et al. |
| 2003/0176776 | A1 | 9/2003 | Huiku |
| 2003/0181799 | A1 | 9/2003 | Lindekugel et al. |
| 2003/0187337 | A1 | 10/2003 | Tarassenko et al. |
| 2003/0195402 | A1 | 10/2003 | Fein et al. |
| 2003/0197679 | A1 | 10/2003 | Ali et al. |
| 2003/0212316 | A1 | 11/2003 | Leiden et al. |
| 2003/0220548 | A1 | 11/2003 | Schmitt |
| 2003/0220576 | A1 | 11/2003 | Diab |
| 2003/0225323 | A1 | 12/2003 | Kiani et al. |
| 2003/0225337 | A1 | 12/2003 | Scharf et al. |
| 2003/0236452 | A1 | 12/2003 | Melker et al. |
| 2003/0236647 | A1 | 12/2003 | Yoon et al. |
| 2004/0006261 | A1 | 1/2004 | Swedlow et al. |
| 2004/0010188 | A1 | 1/2004 | Wasserman et al. |
| 2004/0024297 | A1 | 2/2004 | Chen et al. |
| 2004/0024326 | A1 | 2/2004 | Yeo et al. |
| 2004/0034293 | A1 | 2/2004 | Kimball |
| 2004/0039272 | A1 | 2/2004 | Abdul-Hafiz et al. |
| 2004/0039273 | A1 | 2/2004 | Terry |
| 2004/0054269 | A1 | 3/2004 | Rantala et al. |
| 2004/0054270 | A1 | 3/2004 | Pewzner et al. |
| 2004/0054291 | A1 | 3/2004 | Schulz et al. |
| 2004/0059209 | A1 | 3/2004 | Al-Ali et al. |
| 2004/0059210 | A1 | 3/2004 | Stetson |
| 2004/0064020 | A1 | 4/2004 | Diab et al. |
| 2004/0068164 | A1 | 4/2004 | Diab et al. |
| 2004/0087846 | A1 | 5/2004 | Wasserman |
| 2004/0092805 | A1 | 5/2004 | Yarita |
| 2004/0097797 | A1 | 5/2004 | Porges et al. |
| 2004/0098009 | A1 | 5/2004 | Boecker et al. |
| 2004/0107065 | A1 | 6/2004 | Al-Ali et al. |
| 2004/0116788 | A1 | 6/2004 | Chernoguz et al. |
| 2004/0116789 | A1 | 6/2004 | Boaz et al. |

| | | |
|---|---|---|
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0127779 A1 | 7/2004 | Steuer et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176670 A1 | 9/2004 | Takamura et al. |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230106 A1 | 11/2004 | Schmitt et al. |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0080323 A1 | 4/2005 | Kato |
| 2005/0096516 A1 | 5/2005 | Soykan et al. |
| 2005/0101850 A1 | 5/2005 | Parker |
| 2005/0113543 A1* | 5/2005 | Koberstein et al. ............ 526/318 |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197548 A1 | 9/2005 | Dietiker |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058594 A1 | 3/2006 | Ishizuka et al. |
| 2006/0058683 A1 | 3/2006 | Chance |
| 2006/0064024 A1 | 3/2006 | Schnall |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0155180 A1* | 7/2006 | Brister et al. ............ 600/365 |
| 2006/0195028 A1 | 8/2006 | Hannula et al. |
| 2006/0224058 A1 | 10/2006 | Mannheimer |
| 2006/0239986 A1* | 10/2006 | Perez-Luna et al. ......... 424/94.1 |
| 2006/0247501 A1 | 11/2006 | Ali |
| 2006/0258921 A1 | 11/2006 | Addison et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0129622 A1 | 6/2007 | Bourget et al. |
| 2007/0172904 A1* | 7/2007 | Dementieva et al. ......... 435/7.32 |

FOREIGN PATENT DOCUMENTS

| | | |
|---|---|---|
| EP | 0630203 | 12/1994 |
| EP | 1986543 | 11/2008 |
| JP | 63275325 | 11/1988 |
| JP | 2005034472 | 2/2005 |
| WO | WO9639927 | 12/1996 |
| WO | WO0021438 | 4/2000 |
| WO | WO0140776 | 6/2001 |
| WO | WO0176461 | 10/2001 |
| WO | WO0176471 | 10/2001 |
| WO | WO03039326 | 5/2003 |
| WO | WO2005025399 | 3/2005 |
| WO | WO2006097910 | 9/2006 |

OTHER PUBLICATIONS

Earthrowl-Gould, T., et al.; "Chest and abdominal surface motion measurement for continuous monitoring of respiratory function," Proc. Instn Mech Engrs, V215, Part H; pp. 515-520 (2001).

Yoon, Gilwon, et al.; "Multiple diagnosis based on Photo-plethysmography: hematocrit, SpO2, pulse and respiration," Optics in Health Care and Biomedical optics: Diagnostics and Treatment; Proceedings of the SPIE, vol. 4916; pp. 185-188 (2002).

A. Johansson; "Neural network for photoplethysmographic respiratory rate monitoring," Medical & Biological Engineering & Computing, vol. 41, pp. 242-248 (2003).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Spigulis, Janis, et al.; "Optical multi-channel sensing of skin blood pulsations," Optical Sensing, Proceedings of SPIE, vol. 5459, pp. 46-53 (2004).

Evans, M., et al.; "Alveolar Macrophage Activation in HIV Infection," Journal of Infection, 33, pp. 91-94 (1996).

Nath, N., et al., "Creating 'Smart' Surfaces Using Stimuli Responsive Polymers," Advanced Materials, 14, No. 17, pp. 1243-1247 (2002).

Harmon, M., et al., "A microfluidic actuator based on thermoresponsive hydrogels," Polymer 44, pp. 4547-4556 (2003).

Hilt, J., et al., "Ultrasensitive Biomems Sensors Based on Microcantilevers Patterned with Environmentally Responsive Hydrogels," Biomedical Microdevices, 5:3, pp. 177-184 (2003).

Van Der Linden, H., et al., "Stimulus-sensitive hydrogels and their application in chemical (mico)analysis," The Analyst. 128, pp. 325-331 (2003).

Yu, T., et al., "Methods for the Topographical Patterning and Patterned Surface Modification of Hydrogels Based on Hydroxyethl Methacrylate," Biomacromolecules, 4, pp. 1126-1131 (2003).

"The Application of Metabolomics to Pulmonary Infections," Metabolomics.net, http://www.metabolomics.net/index.aspx?ID=69341, 2 pages (last viewed Apr. 10, 2006).

Tamirisa, P., et al., "Plasma Polymerized Hydrogel Thin Films for Applications in Biosensors," Georgia Institute of Technology (1 page) thesis (2006).

Zhu, H., et al., "Synthesis and functionalization of monodisperse poly(ethylene glycol) hydrogel microspheres within polyelectrolyte multilayer microcapsules," Chem. Commun., pp. 153-155 (2006).

Ciborowski, P., et al., "Investigating the human immunodeficiency virus type 1-infected monocyte-derived macrophage secretome," Virology, 363, pp. 198-209 (2007).

Hollywood, K., et al., "Metabolomics: Current technologies and future trends," Proteomics, pp. 4716-4723 (2006).

Mazurek, S., et al. "The Tumor Metabolome," Institute for Biochemistry and Endocrinology, Veterinary Faculty, Justus-Liebig-University of Giessen, Frankfurter Strasse 100, 35392 Giessen, Germany, Anticancer Research 23:11149-1154 (2003).

* cited by examiner

HYDROGEL THIN FILM FOR USE AS A BIOSENSOR

RELATED APPLICATION

This application claims priority from U.S. Patent Application No. 61/009,721 which was filed on Dec. 31, 2007, and is incorporated herein by reference in its entirety.

BACKGROUND

The present disclosure relates generally to medical devices and, more particularly, to biosensors used to detect molecular markers of pathogen infection associated with various medical conditions.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors may suspect that certain patient conditions are associated with pathogen infection. Identification of a specific pathogen at the source of an infection is challenging for healthcare providers because of the diversity of possible pathogens as well as the nonspecific nature of the symptoms of many infections. However, identification of particular pathogens in infected patients may provide certain treatment advantages. For example, doctors and other healthcare personnel may more easily administer targeted treatments and pharmaceuticals if they know which pathogen is at the source of the infection. Additionally, identification of infecting pathogens in a hospital setting may allow healthcare personnel to track nosocomial infections. It may also be desirable to monitor acute or long-term care patients to prevent new infections in patients with compromised immune systems.

Because of the advantages associated with the specific identification of pathogens, many methods for pathogen detection are currently in use. However, these detection methods are associated with several disadvantages, including extended wait times for results. For example, healthcare providers may attempt to culture particular pathogens from patient samples. Culturing may involve streaking the patient sample across an appropriate solid growth medium, and isolating various organisms within the sample. The culturing process may take days or even weeks depending on the pathogen's growth process. Often, a doctor makes a diagnosis and begins treatment only to later modify this diagnosis and the resulting treatment upon return of the culturing laboratory results. Accordingly, the delay associated with this technique may result in loss of treatment time and waste of hospital resources. Further, not all pathogens may be successfully cultured.

Other methods for identifying specific pathogens include histopathology methods and antibody-based tests. Using histopathology, clinicians may microscopically examine biological samples in order to detect the presence of pathogens. However, this technique involves skilled workers to prepare the samples and to interpret the results. It is also possible to detect a pathogen with an antibody-based test. An antibody-mediated detection mechanism involves detecting a particular protein that is unique to an individual pathogen. Antibody-based tests often involve only a single antibody and are thus limited to detecting only a single type of pathogen. Further, antibody-based tests may also lack sufficient specificity if the targeted antigen has a high degree of homology across species. In such a case, an antibody-based test may provide a false positive result for a particular pathogen Generally, pathogen identification testing is conducted ex vivo, meaning that a biological sample is taken from the body and tested outside of the patient. In vivo testing for pathogen infection provides certain advantages, including more rapid detection of infections as well as increased convenience for the healthcare provider. Although some pathogen identification methods may be used in vivo (i.e. the testing is done in or on the patient's body), such methods are complex and somewhat limited in scope. For example, certain B lymphocytes may be engineered to emit light upon exposure to specific bacteria and viruses. The B lymphocytes may be injected into the bloodstream, and the emitted light may be detected spectroscopically. However, the use of these engineered B lymphocytes is limited to identification of blood-borne pathogens. Further, such a technique is invasive, involving skilled healthcare personnel to prepare the engineered cells and to monitor the injection. A need exists in the art for an effective, specific, and rapid method of identifying pathogens that may be conducted both ex vivo and in vivo.

SUMMARY

Certain aspects commensurate in scope with the present disclosure are set forth below. It should be understood that these aspects are presented merely to provide the reader with a brief summary of certain forms one embodiment might take and that these aspects are not intended to limit the scope of the disclosure. Indeed, the disclosure may encompass a variety of aspects that may not be set forth below.

There is provided a biosensor that includes a hydrogel functionalized with a first affinity molecule with binding specificity for a first pathogen-specific marker; a second affinity molecule with binding specificity for a second pathogen-specific marker; and a third affinity molecule with binding specificity for a third pathogen-specific marker. The biosensor also includes a first indicator capable of producing a first output upon binding of the first affinity molecule with the first pathogen-specific marker; a second indicator capable of producing a second output upon binding of the second affinity molecule with the second pathogen-specific marker; and a third indicator capable of producing a third output upon binding of the third affinity molecule with the third pathogen-specific marker.

There is also provided a method of detecting a pathogen in a biological sample that includes contacting the biological sample with a hydrogel functionalized with a first affinity molecule with binding specificity for a first pathogen-specific marker; a second affinity molecule with binding specificity for a second pathogen-specific marker; and a third affinity molecule with binding specificity for a third pathogen-specific marker. The method also includes detecting an output upon binding of the first, second, and third pathogen-specific markers with respective first, second, and third affinity molecules; and performing an operation on the output to detect the pathogen based upon the presence of the first, second, and third pathogen-specific markers in the biological sample.

There is also provided a system for detecting a pathogen that includes a hydrogel functionalized with a first affinity molecule with binding specificity for a first pathogen-specific marker; a second affinity molecule with binding specificity for a second pathogen-specific marker; and a third affinity molecule with binding specificity for a third pathogen-specific marker. The system also includes a first indicator capable of producing a first output upon binding of the first affinity molecule with the first pathogen-specific marker; a second indicator capable of producing a second output upon binding of the second affinity molecule with the second pathogen-specific marker; a third indicator capable of producing a third output upon binding of the third affinity molecule with the third pathogen-specific marker; and a monitor operatively coupled to the first indicator, the second indicator, and the third indicator, wherein the monitor is configured to receive the first output, the second output, and the third output and perform an operation to determine if the pathogen is present in a biological sample.

BRIEF DESCRIPTION OF THE DRAWINGS

Advantages of the present disclosure may become apparent upon reading the following detailed description and upon reference to the drawings in which.

DETAILED DESCRIPTION

Figure 1:
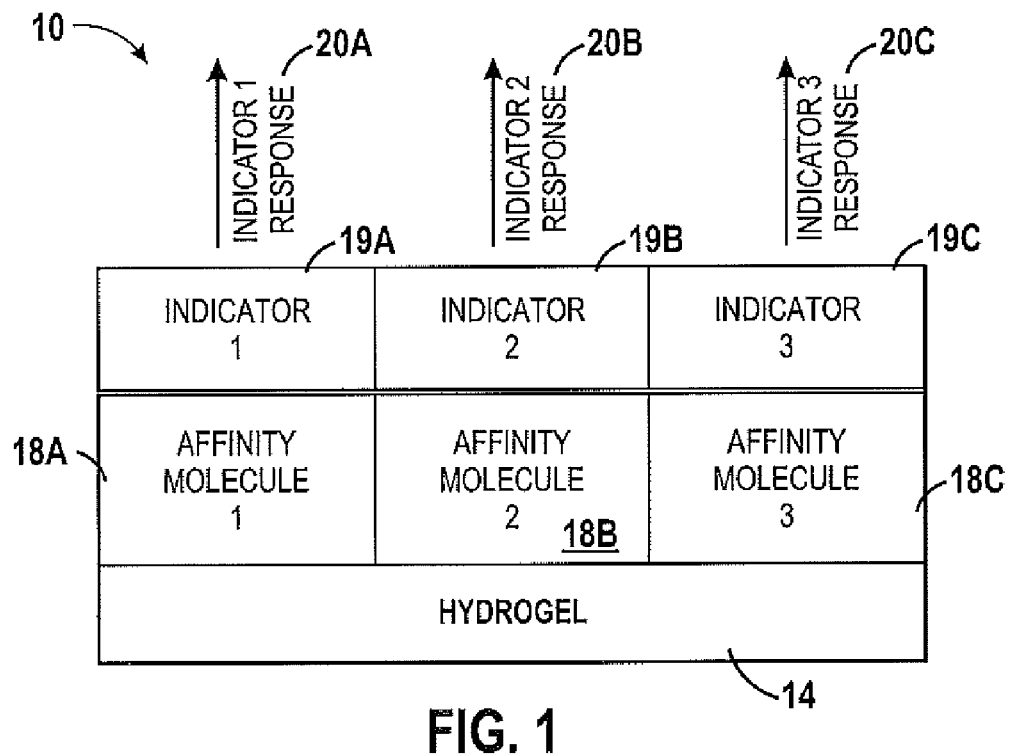
FIG. 1 is a schematic cross-section of a biosensor capable of producing an indicator response according to the present disclosure.

One or more embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A biosensor is provided herein that may assess a biological sample and is capable of producing feedback such that detection of a specific pathogen is made possible. Such a biosensor provides significant time advantages, as pathogen or metabolome detection of pathogens may occur in a fraction of the time associated with other techniques. A biosensor according to the present disclosure may include a hydrogel, which may be composed of molecules with large molecular mass composed of repeating structural units, or monomers connected by covalent chemical bonds, i.e., a network of polymer chains. In one embodiment, the hydrogel may be functionalized with specific affinity molecules, i.e., molecules that have a specific affinity for a particular protein or metabolite. For example, an antibody or other affinity molecule may be disposed on the surface of the hydrogel. An antibody may have a specific affinity for a corresponding pathogenic antigen. In one embodiment, the antigen may be a protein made by a pathogen. In other embodiments, the antigen may be a human protein generated within the cell as a result of cell metabolism due to a viral or intracellular bacterial infection. The functionalized hydrogel may be then contacted with a biological sample and binding will occur if the antigen exists in the biological sample. In addition, the biosensor according may be capable of producing an indicator response upon binding of one or more metabolites or proteins with corresponding specific affinity molecules, allowing for the detection of a specific pathogen.

It is envisioned that the detection of multiple (i.e. three or more) markers that are specific for a given pathogen may increase the specificity of a sensor as provided herein. It should also be understood that a sensor may detect three or more, e.g., 10, 20, 50, or even more than 100, different markers of a particular pathogen. Further, a sensor may include affinity molecules specific for at least one or multiple different pathogens. In one embodiment, such as those specific for the detection of pathogens via their metabolic footprints, it may be advantageous to use 50 or more different affinity molecules in order to assess a wide range of metabolites that may be common to many different pathogens. However, the individual combination of many different individual metabolites may be generally specific to a particular pathogen.

FIG. 1 is a schematic cross-section of a biosensor 10 capable of providing an indicator response 24. A biological sample may be contacted with the biosensor 10 The biological sample may include a blood product, a tissue sample, semen, mucous, sputum, saliva, pus, urine, or the like. In the illustrated embodiment, the biosensor 10 includes a hydrogel 14 with three or more affinity molecules 18 specific for respective three or more pathogen markers. The hydrogel 14 may be functionalized with the specific affinity molecules 18 (e.g., 18A, 18B and 18C) that are either disposed on the surface of the hydrogel 14 or are embedded with the hydrogel 14 as part of the polymer. The biosensor 10 also includes indicators 19 (e.g., 19A, 19B and 19C) adapted to detect the binding of the respective pathogen markers with corresponding affinity molecules 18. The result of the detection may be an indicator response 20 (e.g. 20A, 20B and 20C). This indicator response 20 provides a downstream message to a healthcare provider that relates to the pathogen, ultimately allowing for pathogen detection in the biological sample.

In one embodiment, the hydrogel 14 may be disposed on a substrate (not shown). The substrate may be made from any material that may be capable of supporting the hydrogel 14. For example, the substrate material may include insulating materials, semiconductive materials, electrically conducting materials, organic polymers, biopolymers, paper, membrane, a composite of metal and polymers, or any combinations thereof. Exemplary insulating materials include glass, such as silicon oxide and ceramic. Exemplary semiconductive materials include doped or undoped silicon or GaAs. Exemplary electrically conducting materials are metals, such as nickel, brass, steel, aluminum and gold or electrically conductive polymers. In one embodiment, the substrate may be non-porous and substantially rigid to provide structural stability. In another embodiment, the substrate may be microporous or porous.

The hydrogel 14 may be connected to the substrate through any reagent and or reagents that may be coupled, e.g., covalently, to the substrate surface to anchor the hydrogel to the substrate. The anchor reagent enables attachment of the hydrogel 14 to the surface of the substrate and may be any molecule able to interact with a molecule attached to a hydrogel 14. For example, suitable anchor reagents may include silanes such as (3-acryloxypropyl)trimethoxysilane. In some embodiments the anchor reagent moiety may be a polymerizable moiety (hereafter "a first polymerizable moiety") that is able to cross-link to a second polymerizable moiety attached to a hydrogel. In exemplary embodiments, the first and second polymerizable moieties may include methacryl, acryl, allyl or vinyl.

The hydrogel 14 may be disposed on the substrate in any suitable thickness, depending on the desired binding capacity of the biosensor 10. For example, the hydrogel 14 may be less than one micrometer thick, about 1 micrometer thick, at least about 10 micrometers thick, at least about 20 micrometers thick, at least about 50 micrometers thick, or at least about 100 micrometers thick. It should be understood that the response time of the sensor 10 may be related to the thickness of the hydrogel 14. For example, a thinner hydrogel 14 may have a faster response time than a relatively thicker hydrogel 14.

In one embodiment, a detection mechanism provides the indicator response 20 upon binding of a pathogen-specific marker to an affinity molecule 18. Upon binding of the target molecule to the affinity molecule 18, a change takes place in the biosensor 10, resulting in either an optical, chemical, electrochemical, or electrical change in the hydrogel 14 or the affinity molecule 18 that may be transmitted downstream for further analysis. For example, as depicted, an affinity molecule may be linked to a downstream indicator 19, such as an enzyme capable of catalyzing a reaction that ultimately results in a local increase in fluorescence that may be spectroscopically detected. It is envisioned that certain detection mechanisms may be employed for in vivo or ex vivo detection of binding. For example, suitable detection mechanisms may include detection of fluorescence, luminescence, chemiluminescence, absorbance, and/or reflectance. Alternatively, the detection mechanism may involve detection of a change in the electrical state of the hydrogel 14, such as a change in charge or impedance. Alternatively, certain detection mechanisms may be suitable for use in ex vivo embodiments. In such an embodiment, the biological sample may be removed form the body for analysis. Such detection mechanisms may include, for example, gas phase ion spectrometry, atomic force microscopy, radio frequency mass spectrometry, multipolar coupled resonance spectroscopy, laser desorption/ionization (MALDI, SELDI), fast atom bombardment, plasma desorption and secondary ion mass spectrometers.

The indicator response 20 produced by the detection mechanism may be processed to produce a downstream indication of pathogen detection. In one embodiment, the output of the indicator response 20 may be a display listing the pathogen-specific markers identified by the detection mechanism upon binding. The display may be viewed on a computer screen, a hand-held device or the like. In this example, pathogen or metabolome detection may occur when a skilled technician views the display, and interprets the presence of such a collection of metabolites present in the biological sample to yield a certain result.

Figure 2:
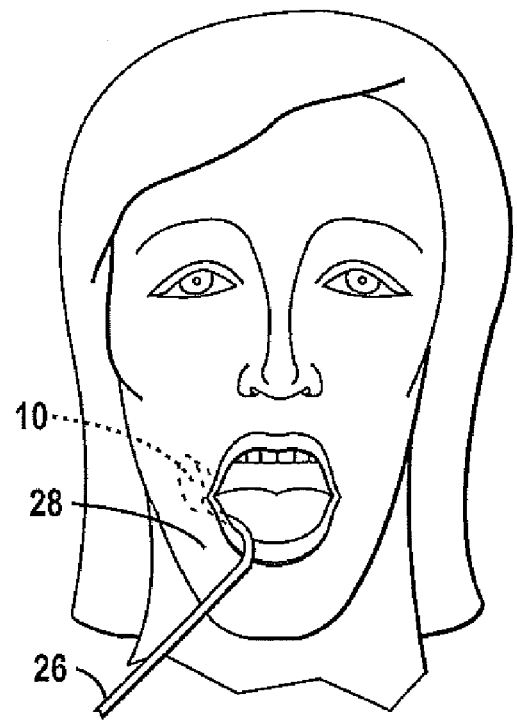
FIG. 2 illustrates a perspective view of a patient using a sensor for in vivo detection of a pathogen according to the present disclosures.

In one embodiment, it may be advantageous to provide a biosensor 10 for use on buccal or sublingual tissue 28 that may be easily reached by the patient or a healthcare worker. For example, FIG. 2 illustrates a perspective view of a patient using a biosensor 10 for in vivo detection of a pathogen. FIG. 2 illustrates the placement of a biosensor 10 on a buccal surface 28 in order to assess the presence of a pathogen in the tissue, blood, or interstitial fluid. For example, the biosensor 10 may be used to detect the presence of candidiasis, commonly called yeast infection or thrush, which is a fungal infection sometimes found in the mouth. Or, as another example, the biosensor 10 may be used to detect *streptococcus mutans*, a bacterium commonly found in the mouth and that is a significant contributor to tooth decay. Specifically, FIG. 2 shows an embodiment of a biosensor 10 including a lead 26 in communication with the biosensor 10. In this particular embodiment, the lead 26 may be capable of transmitting an electrical feedback from the biosensor 10 to the monitor (not shown) such that an indicator response 32 may be displayed. The biosensor 10 and lead 26 may be suitably sized and shaped such that a patient may easily close his or her mouth around the sensor with minimal discomfort. Additionally, the biosensor 10 may be suitably sized and shaped to allow the biosensor 10 to be positioned near or flush against the buccal tissue 28.

In the embodiment illustrated by FIG. 2, since biosensor 10 may be used for in vivo detection of pathogen infection, it is envisioned that the biosensor 10 may be useful for monitoring patients who are in the hospital long-term. The sensor 10 may be secured to the oral or nasal mucosal tissue with a mucoadhesive or other suitable mounting device, such as a clip. The mucoadhesive layer may be applied to the hydrogel 14. In one embodiment, the hydrogel 14 itself may include a mucoadhesive. In such an embodiment, direct application to the sensor 10 to mucosal tissue may securely affix the sensor 10 to the tissue. The term mucoadhesive refers to a substance that sticks to or adheres to the mucous membrane by any number of mechanisms, for example, but not limited to the following: hydrogen-bonding, ionic interaction, hydrophobic interaction, van der Waals interaction, or combinations thereof.

The mucoadhesive layer may include a variety of mucoadhesive compositions to secure electrodes to mucosal tissue. As one of ordinary skill in the art may recognize, the mucoadhesive substance may allow electrical signals to be conducted and received from the mucosal tissue to the electrodes. Suitable mucoadhesives include, but are not limited to, hydroxypropyl cellulose, hydroxypropyl methylcellulose, hydroxyethylcellulose, ethylcellulose, carboxymethylcellulose, dextran, guar gum, polyvinyl pyrrolidone, pectins, starches, gelatin, casein, acrylic acid polymers, polymers of acrylic acid esters, vinyl polymers, vinyl copolymers, polymers of vinyl alcohols, alkoxy polymers, polyethylene oxide polymers, polyethers, and any combination of the above.

In one embodiment, the mucoadhesive may be a biocompatible polymer, for example polyacrylic acid, that may be cross-linked with an acceptable agent to create a hydrogel 14. The use of an insoluble gel may be desirable, particularly for long term monitoring, since it remains adhered to the mucosal tissue for relatively long periods of time. Cross-linked polyacrylic acid polymers may be appropriate for use for three to five days or even longer. Certain polymers available from Noveon, Inc. (Wickliffe, Ohio) and CarboMer, Inc, (San Diego, Calif.) are weak acids and contain many negatively-charged carboxyl-groups. The multiple negative charges on these polymers promote hydrogen-bonding between the polymers and the negatively charged mucin, a glycoprotein that mediates attachment of mucus to the epithelial lining. A mucoadhesive polymer may also include acrylic acid polymers (e.g. Carbopol® 940, also known as Carbomer® 940, Carbopol 934P and Carbopol® 980, products of BF Goodrich), methyl vinyl/maleic acid copolymers (e.g. Gantrez® S-97, a product of International Specialty Products), polyvinyl pyrrolidone also known as povidone (e.g. Plasdone® K-90, a product of International Specialty Products). These polymers impart relatively high viscosity at relatively low concentrations. They may be incorporated onto a sensor in amounts ranging from about 0.01% to about 10% by weight relative to the total composition, for example. These viscosity modifying agents further act to improve the film adhesion of the composition to mucous membranes. Carbopol® 980, in one embodiment, may be 2-3% by weight of the total composition.

Figure 3:
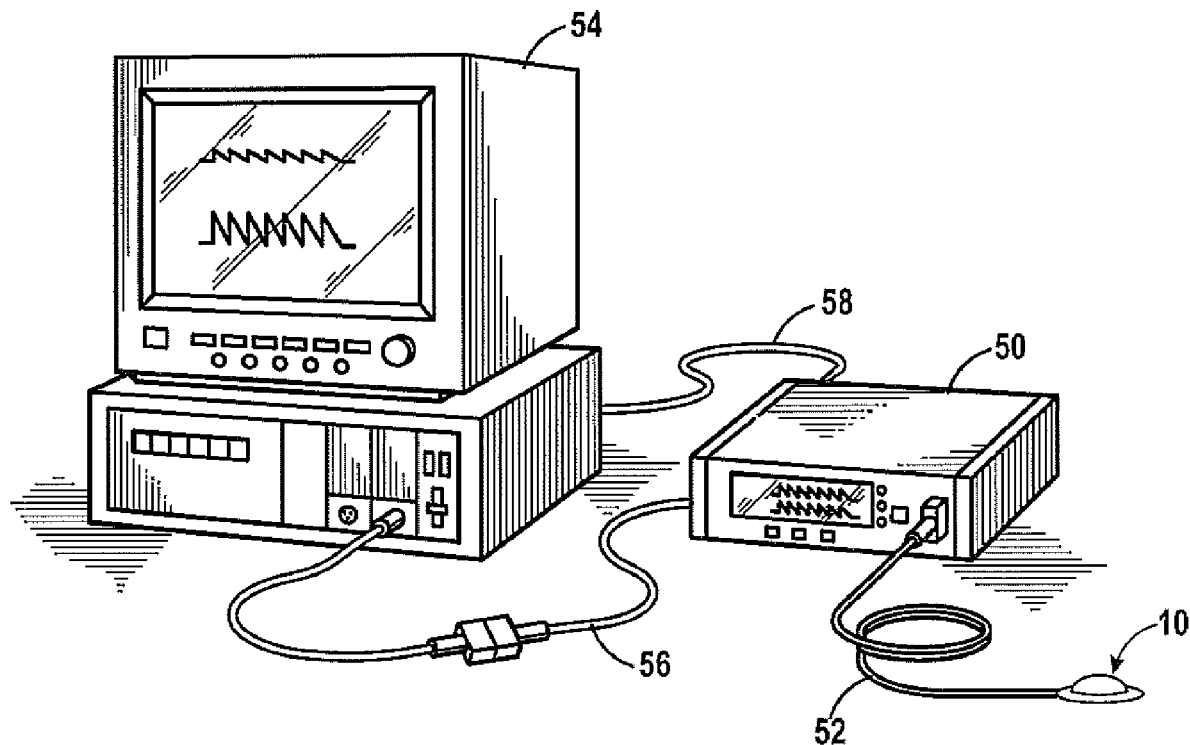
FIG. 3 illustrates a perspective view of a monitoring system according to the present disclosures.

As noted, the output of the sensor 10 may be sent to a monitor. FIG. 3 depicts a system including a sensor 10 coupled to a patient monitor 50 that may display information related to the output of the sensor 10. It should be appreciated that the cable 52 of the sensor 10 may be coupled to the monitor 50 or it may be coupled to a transmission device (not shown) to facilitate wireless transmission between the sensor 10 and the monitor 50. Furthermore, to upgrade pathogen detection provided by the monitor 50 to provide additional functions, the monitor 50 may be coupled to a multi-parameter patient monitor 54 via a cable 56 connected to a sensor input port or via a cable 58 connected to a digital communication port. For example, it is envisioned that pathogen detection as provided herein may be part of a larger patient monitoring strategy that includes monitoring of heart rate, blood pressure and/or blood oxygen saturation, although other physiological parameters may be monitored as well.

The analysis of the output may include a threshold comparison to the raw binding data. For example, if the affinity molecule is an antibody and the pathogen-specific marker binding detection includes a fluorescence change, the change in fluorescence may be analyzed and correlated to previously determined thresholds. It is envisioned that each affinity molecule may provide a separate output to the monitor 50. Each output may be compared to a threshold to determine if the levels of pathogen-specific marker in the biological sample indicate that the pathogen is present. Further, because sensor 10 may produce multiple outputs, each specific to a different affinity molecule 18, these outputs may be combined to provide a statistical likelihood of pathogen presence in the biological sample. In the corresponding embodiment, a threshold may be established for an alarm if it is likely that a certain pathogen may be present in the biological sample.

Figure 4:
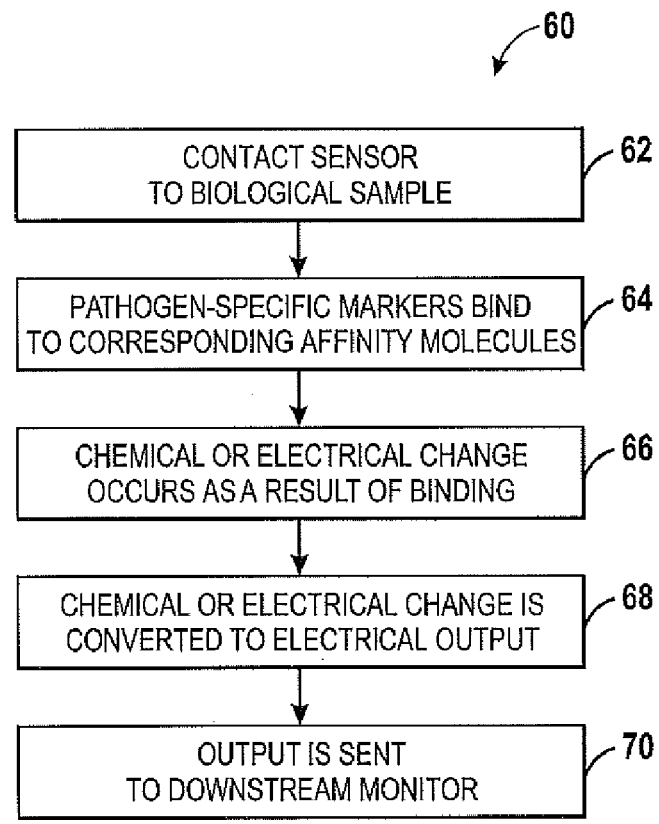
FIG. 4 is a flow chart illustrating the method of pathogen detection in accordance with one aspect of the present disclosures.

FIG. 4 is a flow chart illustrating a process 60 of pathogen detection. In this illustration, the method of detection begins at step 62, where the biological sample 12 may be contacted with the biosensor 10. At step 64, pathogen-specific markers present in the biological sample 12 may bind to a corresponding affinity molecule 18 (e.g., 18A, 18B, and 18C). At step 66, detection of binding occurs. In this exemplary embodiment, detection may occur by way of enzyme linked immunosorbent assays (ELISA). After binding of the pathogen-specific markers to the affinity molecules 18, an enzymatic substrate produces a visible signal, which indicates the quantity of pathogen-specific marker in the sample. The visible signal may be sensed spectroscopically and converted to an electrical output at step 68. At step 70, an indicator response 20 may be sent downstream to a processor, such as a processor associated with a monitor 50.

1. Hydrogels

The hydrogel 14 may be a cross-linked polymeric material that swells in water but does not dissolve. It is envisioned that the hydrogel 14 may be capable of absorbing at least 1 to 10 times, and in one embodiment at least 100 times, its own weight of a liquid The hydrogel chosen for use in the biosensor 10 should depend directly on the method of functionalization. It is envisioned that the hydrogel 14 may be biocompatible.

In some embodiments, the hydrogel 14 may be polymerized from acrylic monomers. The acrylic monomer may be selected from the group consisting of acrylamido-glycolic acid, acrylamido-methyl-propa-ne-sulfonic acid, acrylamido-ethylphosphate, diethyl-aminoethyl-acrylamide-, trimethyl-amino-propyl-methacrylamide, N-octylacrylamide, N-phenyl-acrylamide and tert-butyl-acrylamide. In embodiments in which the device contains a cross-linking agent, exemplary cross-linking agents may be N,N'-methylene-bisacrylamide, N,N'-methylene-bismethacrylamide, diallyltardiamide and poly(ethylene glycol)dimethacrylate. Examples of suitable hydrogels may also include silicon wafers, borosilicate glass substrates, 2-hydroxyethyl methacrylate (HEMA), N-Isopropylacrylamide (NIPAAm), and polyethylene glycol (PEG).

The hydrogel may include any number of molecules. For example, the hydrogel may include a polymerized monomer or hydrogel a cross linking agent and optionally a chemical or UV-light activated inducer agent. Examples of such monomers or dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycoldimethacrylate, N,N'-methylenebisacrylamide, polyethyleneglycoldiacrylate (PEGDA), polyethyleneglycoldimethacrylate (PEGDMA), polyethyleneglycoldiacrylate (PEGDA), polyethyleneglycoldimethacrylate (PEGDMA), poly(vinyliden fluoride) (PVdF) based polymer, a polyacrylonitrile (PAN) based polymer, a polymethylmethacrylate (PMMA) based polymer, a polyvinyl chloride (PVC) based polymer, and a mixture of the poly(vinyliden fluoride) (PVdF) based polymer, polyacrylonitrile (PAN) based polymer, polymethylmethacrylate (PMMA) based polymer, and polyvinyl chloride (PVC) based polymer, and mixtures thereof.

Cross linking agents and optionally the chemical or UV-light activated inducer agent may include N,N'-methylenebisacrylamide, methylenebismethacrylamide ethyleneglycoldimethacrylate and agent N,N'-methylenebisacrylamide. Irgacure 2959 (Ciba); 2,2-dimethoxy-2-phenylacetophenone, 2-methoxy-2-phenylacetone, benzyl-dimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1,1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyltioxantone, chloro tioxantone, 2,2-chlorobenzophenone, benzyl benzoate, and benzoyl benzoate, TEMED, and ammonium persulfate (APS).

In one embodiment, the hydrogel 14 may be polymerized in place over a substrate. The in situ polymerization process provides several advantages. First, the amount of hydrogel materials may be readily controlled by adjusting the amount of a monomer solution placed on the substrate surface, thereby controlling the amount of binding functionalities available. For example, the amount of a monomer solution deposited onto the substrate surface may be controlled by using methods such as pipetting, ink jet, silk screen, electro spray, spin coating, or chemical vapor deposition. Additionally, the hydrogel 14 may be polymerized to form a coating over the substrate or may be lifted off of the substrate after polymerization. For in situ polymerization, photoinitiation or thermal initiation of polymerization may be used. The monomer solution may be deposited onto a substrate and in situ polymerized on the substrate surface by irradiating, e.g., by UV exposure, for example. The monomer mixture solution may be subsequently dried by any of the known methods such as air drying, drying with steam, infrared drying, vacuum drying, etc. In a specific embodiment, monomer 2-hydroxyethyl methacrylate (HEMA) may be cross-linked with 2% ethylene glycol dimethacrylate and photoinitiator 2,2'-dimethoxy-2-phenylacetophenone is polymerized between two silicon wafers.

In one particular embodiment, functionalization of the hydrogel 14 may take place after polymerization. The hydrogel 14 may be functionalized with one or more specific affinity molecules 18 with affinity for one or more unique metabolites. Specifically, in one embodiment, functionalization takes place in particular regions of the hydrogel. The hydrogel 14 may be functionalized by a number of techniques including plasma polymerization, soft lithography, and photopolymerization. Soft lithography refers to a set of methods for fabricating or replicating structures using elastomeric stamps, molds, and conformable photomasks. This method may be generally used to construct features measured on the nanometer scale. In this process, a desired pattern may be etched onto a substrate (usually silicon), a stamp may be created, and then the single-molecule layer of ink from the stamp may be applied to the surface of the substrate. In one embodiment, the monomers of the hydrogel 14 may be functionalized with the affinity molecules 18 prior to polymerization.

2. Formation of a Phase-Change Hydrogel

Certain polymers reversibly change conformation in response to a specific external stimulus. For example, almost all polymers undergo some reversible conformational change with changes in solvents, and some, such as poly N-isopropylacrylamide, undergo conformational changes in response to temperature changes. Solutes that interact with the side groups on the polymer backbone may also induce conformational changes; introduction of ionized groups onto the backbone of the polymer thus sensitizes the polymer conformation to changes in ionic strength. Polymers that change conformation in response to increased concentrations of certain elements in a solute may be prepared by adding to that polymer a functional group that selectively interacts with that element. For example, a hydrogel 14 may be prepared with a negatively charged group that may form chemical associations with a positively charged group present in a solute. Such polymers may be further mixed with crosslinking agents to form gels that exhibit the same response to stimuli as the polymer from which they are formed. For example, these gels may undergo volume changes at conditions when the constituent polymer chains change conformation. Volume changes between 0.1 and 50%, or even greater, are contemplated by the present disclosure.

In one embodiment, the sensor 10 may include a hydrogel 14 with phase-transition properties. Such a hydrogel may have dispersed with it electrically conductive particles. When the pathogen-specific marker binds to the gel matrix, it causes a change in the hydrophilicity of the matrix, and therefore changes the swelling properties of the gel. As the hydrogel shrinks and swells, the electrically conductive particles embedded in the hydrogel move, respectively, closer to and farther from one another. Depending on the pore size of the hydrogel, the electrically conductive particles may move close enough together to conduct a current, which may be detected by electrodes that are disposed on or embedded in the hydrogel 14. The conductive bodies embedded in the polymer may be in the form of particles or fibers and may include carbon, such as carbon black, coated carbon, graphite, coated graphite, metal, alloy and ceramic materials. In some embodiments, the hydrogel 14 includes electrically conductive bodies in the concentration of at least 0.5% to 50% by weight.

In addition, a monomer component may be added to change the sensitivity of the device by making the hydrogel even more hydrophobic or hydrophilic, as desired by the needs of the user. The more hydrophobic the gel, the more it may tend to stay in a collapsed or shrunken state. For example, an acrylamide, which may be more hydrophilic than NIPA, may be added, or N-butylacrylamide, which may be more hydrophobic than NIPA, may be added to adjust the properties of the hydrogel. In one embodiment, the electrically conductive particles may form a crystalline colloidal array as set forth in U.S. Patent Publication No. 20060024813, the specification of which is hereby incorporated by reference in its entirety for all purposes. The electrically conductive particles may be added to a monomer solution to form a hydrogel 14 with the particles dispersed therein.

3. Fluorescence Resonant Energy Transfer (FRET) for the Detection of Antigen-Antibody Binding to a Hydrogel In one embodiment, the sensor 10 may employ FRET to detect the binding of a pathogen-specific marker to an affinity molecule 18. In this embodiment, the affinity molecule 18 may be tagged with two fluorescent dyes, a donor and an acceptor. For example, one dye may be coupled to the affinity molecule 18 and the other may be coupled to the hydrogel 14. The dyes fluoresce in a narrow range of wavelengths (their emission spectra) when they receive energy in another range of wavelengths (their absorption spectra). The absorption spectrum of the acceptor fluorescent dye may overlap the emission spectrum of the donor fluorescent dye.

In operation, the sensor 10 may include a light source, such as an LED, for emitting energy toward the pathogen-specific marker detector at a wavelength that may be within the absorption spectrum of the donor fluorescent dye. In response, the donor fluorescent dye fluoresces energy at a wavelength within its emission spectrum. When the pathogen-specific marker is not bound to the affinity molecule, the donor and acceptor fluorescent dyes may not be in sufficient proximity such that emission of energy from the donor fluorescent dye may cause the acceptor fluorescent dye to fluoresce. When an affinity molecule binds to the pathogen-specific marker, however, the affinity molecule 18 undergoes a conformational change that brings the dyes into sufficient proximity to allow FRET to occur. When the dyes are sufficiently proximate and properly oriented, the emission of energy by the donor fluorescent dye causes the acceptor fluorescent dye to fluoresce. As a result, the energy emitted by a sensor depends upon whether the pathogen-specific marker may be bound to affinity molecule 18.

A light detector may receive the light fluoresced by the acceptor dye, and a downstream processor monitors the received light. In particular, the processor monitors the intensity of energy emitted in the emission spectrum of the donor fluorescent dye, in relation to the intensity of energy emitted in the emission spectrum of the acceptor fluorescent dye. The relative intensity of energy at these two wavelengths may be a function of the number of affinity molecules 18 having pathogen-specific marker bound to them, which in turn may be a function of the concentration of the pathogen-specific marker in the body of the patient.

In one embodiment, a donor fluorescent dye may be fluorescein 5-isothiocyanate (FITC). Receiving energy at a wavelength of 494 nm, FITC fluoresces energy at wavelength range of 516-525 nm (or about 520 nm). In this embodiment, the acceptor fluorescent dye includes tetramethylrhodamine 5 (and 6)-isothiocyanate (TRITC). Receiving energy at a wavelength range of 516-525 nm, TRITC fluoresces energy at a wavelength range of 570-580 nm (or about 574 mm). TRITC does not substantially fluoresce in response to energy received at a wavelength of 494 nm, because this wavelength may be outside the excitation spectrum of TRITC.

4. Affinity Molecules and Pathogen-Specific Markers

An affinity molecule 18 may be a biomolecule that selectively binds a specific chemical species as part of its biological function. This component may be bound to the gel directly or by one or more linking molecules. Examples of such affinity molecules 18 nucleic acids, nucleotide, nucleoside, nucleic acids analogues such as PNA and LNA molecules, proteins, peptides, antibodies including IgA, IgG, IgM, IgE, enzymes, enzymes cofactors, enzyme substrates, enzymes inhibitors, membrane receptors, kinases, Protein A, Poly U, Poly A, Poly lysine, triazine dye, boronic acid, thiol, heparin, membrane receptors, polysaccharides, coomassie blue, azure A, metal-binding peptides, sugar, carbohydrate, chelating agents, prokaryotic cells and eukaryotic cells, antigens, porphyrins, ferritin, or pheromone receptors. A sensor 10 a provided herein may therefore include one or more linking molecules that bind the affinity molecule 18 to the gel monomer. In addition, the affinity molecule 18 may be modified by being reacted with a molecule that may be bound to the linking agent, or to the gel itself. An example of a linking molecule may be 5-(biotinamido)pentylamine.

In one embodiment, an antibody may be linked to a gel monomer to form a hydrogel that binds an antigen. As above, the sensitivity of the sensor may be adjusted to the desired concentration by modifying the ratio of gel monomer to recognition component, the degree of crosslinking and the hydrophobicity of the gel monomer. Hydrophobicity may be adjusted as discussed above with the addition of another monomer that may be either more or less hydrophobic than the gel monomer, depending on the needs of the user.

By "pathogen-specific marker," it may be meant any molecule, compound or particle to be detected by the affinity molecule. Suitable pathogen-specific markers may include organic and inorganic molecules, as well as biomolecules. In one embodiment, the pathogen-specific marker may be a protein. As will be appreciated by those in the art, there are a large number of possible proteinaceous pathogen-specific markers that may be detected. By "proteins," it may be meant proteins, oligopeptides and peptides, derivatives and analogs, including proteins containing non-naturally occurring amino acids and amino acid analogs, and peptidomimetic structures.

The biosensor 10 may be envisioned to have the ability to detect molecular markers of pathogen infection. Examples of pathogens may include bacteria, viruses, and fungi. In addition to detecting foreign proteins, the biosensor 10 may also be used to detect human proteins that are up-regulated as a result of pathogen infection. Appropriate pathogen-specific markers may include the secretome of a human or pathogenic cell. The secretome is a term describing part or all the proteins actively secreted by a cell. For example, neopterin is a protein produced by macrophages following stimulation by interferon gamma secreted by stimulated T-lymphocytes. Serum neopterin increases as the HIV disease progresses and may be a prognostic marker for progression to AIDS. Thus, the biosensor 10 may be used to detect the presence of neopterin, which serves as a surrogate marker for active alveolar macrophages. Additionally, the biosensor 10 may also detect a number of proteins that expressed differently in HIV-infected patients, such as cystatin B, cystatin C, L-plastin, LTA4H, α-enolase, and chitinase 3-like 1 protein (HC-gp39).

The sensor 10 may also detect the secretome of *Plasmodium falciparum*, the major malaria parasite. In this embodiment, the affinity molecules 18 may have specific affinity for an N-terminal sequence common to many known secreted proteins of malaria. The sequence, known as the *plasmodium* export element, or pexel sequence, includes a highly conserved 5 amino-acid sequence RXLXE/Q.

In other embodiments, the sensor 10 may include affinity molecules 18 with affinity to certain metabolic products. In such an embodiment, pathogens may be identified through their metabolic profiles. A metabolome refers to the complete set of small-molecule metabolites (such as metabolic intermediates, hormones and other signalling molecules, and secondary metabolites) to be found within a biological sample. Although many pathogens, such as bacteria, have certain metabolic products in common, these pathogens nonetheless may be differentiated by examining certain characteristic combinations of metabolic products. For example, the metabolic profile of *Heliobacter pylori* has been established. Accordingly, a sensor 10 may include affinity molecules 18 specific for a minimal number of unique metabolites of *H. pylori*.

While the disclosure may be susceptible to various modifications and alternative forms, specific embodiments have been shown by way of example in the drawings and have been described in detail herein. However, it should be understood that the disclosure is not intended to be limited to the particular forms disclosed. Indeed, the present disclosure may not only be applied to sensors for pathogen identification, but may also be utilized for the measurement and/or analysis of other pathogen-specific markers found in patient tissue. Rather, the disclosure is to cover all modifications, equivalents, and alternatives falling within the spirit and scope of the disclosure as defined by the following appended claims. It will be appreciated by those working in the art that the sensors fabricated using the present disclosure may be used in a wide variety of contexts, such as the detection of cancer or metabolic disorders.

What is claimed is:

1. A biosensor for detecting a pathogen comprising:
a hydrogel functionalized with:
  a first affinity molecule with binding specificity for a first pathogen specific marker;
  a second affinity molecule with binding specificity for a second pathogen-specific marker; and
  a third affinity molecule with binding specificity for a third pathogen-specific marker;
a first indicator capable of producing a first output upon binding of the first affinity molecule with the first pathogen-specific marker;
a second indicator capable of producing a second output upon binding of the second affinity molecule with the second pathogen-specific marker; and
a third indicator capable of producing a third output upon binding of the third affinity molecule with the third pathogen-specific marker, wherein at least one of the first, second, or third outputs comprises an electrical output.

2. The biosensor in claim 1, wherein the biosensor comprises an adhesive configured to affix the biosensor to a patient.

3. The biosensor recited in claim 1, wherein the first, second, and third pathogen-specific markers are metabolic products of the pathogen.

4. The biosensor recited in claim 1, wherein at least one of the first, second, or third outputs comprises a change in electrical impedance of the hydrogel triggered by binding of the respective first, second, or third pathogen-specific marker.

5. The biosensor recited in claim 1, wherein at least one of the first, second, or third pathogen-specific markers is specific to *helicobacter pylori*.

6. The biosensor recited in claim 1, wherein the first, second, and third pathogen-specific markers are part of a secretome of the pathogen.

7. The biosensor recited in claim 6, wherein the first, second, and third pathogen-specific markers are part of the secretome of *Plasmodium falciparum*.

8. The biosensor recited in claim 6, wherein the first, second, and third pathogen-specific markers comprise proteins having the pexel/vacuolar transport signal.

9. The biosensor recited in claim 1, wherein at least one of the first, second, or third affinity molecules is an antibody.

10. The biosensor recited in claim 1, wherein the first affinity molecule is disposed on a first region of the hydrogel, the second affinity molecule is disposed on a second region of the hydrogel, and a third affinity molecule is disposed on a third region of the hydrogel.

11. The biosensor recited in claim 1, wherein the hydrogel comprises 2-hydroxyethyl methacrylate or N-Isopropylacrylamide.

12. The biosensor recited in claim 1, wherein the hydrogel comprises a mucoadhesive.

13. A system for detecting a pathogen comprising:
a hydrogel functionalized with:
a first affinity molecule with binding specificity for a first pathogen-specific marker;
a second affinity molecule with binding specificity for a second pathogen-specific marker; and
a third affinity molecule with binding specificity for a third pathogen-specific marker;
a first indicator capable of producing a first output upon binding of the first affinity molecule with the first pathogen-specific marker;
a second indicator capable of producing a second output upon binding of the second affinity molecule with the second pathogen-specific marker;
a third indicator capable of producing a third output upon binding of the third affinity molecule with the third pathogen-specific marker, wherein at least one of the first, second, or third outputs comprises an electrical output; and
a monitor operatively coupled to the first indicator, the second indicator, and the third indicator, wherein the monitor is configured to receive the first output, the second output, and the third output and perform an operation to determine if the pathogen is present in a biological sample.

14. The system recited in claim 13, comprising an alarm that is adapted to be triggered upon detection of the pathogen.

15. The system recited in claim 13, wherein the hydrogel is disposed on a surface of the biosensor adapted to directly contact a patient.

* * * * *